United States Patent
Su

(10) Patent No.: US 6,198,962 B1
(45) Date of Patent: Mar. 6, 2001

(54) QUADRATURE DETECTION COIL FOR INTERVENTIONAL MRI

(75) Inventor: Sunyu Su, South San Francisco, CA (US)

(73) Assignee: Toshiba America MRI, Inc., Tustin, CA (US)

( * ) Notice: Subject to any disclaimer, the term of this patent is extended or adjusted under 35 U.S.C. 154(b) by 0 days.

(21) Appl. No.: 09/199,411

(22) Filed: Nov. 25, 1998

(51) Int. Cl.[7] .................................................. A61B 5/055
(52) U.S. Cl. ........................... 600/422; 324/318; 324/322
(58) Field of Search ................................... 324/318, 322; 600/410, 421, 422

(56) References Cited

U.S. PATENT DOCUMENTS

| | | |
|---|---|---|
| 5,129,911 | 7/1992 | Siczek et al. . |
| 5,277,183 * | 1/1994 | Vij ........................................ 324/318 |
| 5,357,958 | 10/1994 | Kaufman . |
| 5,363,845 | 11/1994 | Chowdhury et al. . |
| 5,379,767 * | 1/1995 | Derby et al. ........................... 600/422 |
| 5,386,191 | 1/1995 | McCarten et al. . |
| 5,386,447 | 1/1995 | Siczek . |
| 5,437,280 | 8/1995 | Hussman . |
| 5,445,153 * | 8/1995 | Sugie et al. ........................... 324/318 |
| 5,500,594 | 3/1996 | Leussler . |
| 5,515,855 | 5/1996 | Meyer et al. . |
| 5,517,120 | 5/1996 | Misic et al. . |
| 5,534,778 | 7/1996 | Loos et al. . |
| 5,565,780 | 10/1996 | Derby . |
| 5,569,266 | 10/1996 | Siczek . |
| 5,592,088 | 1/1997 | Matsunaga et al. . |
| 5,594,342 * | 1/1997 | Brey et al. ........................... 324/322 |
| 5,595,177 | 1/1997 | Mena et al. . |
| 5,602,479 | 2/1997 | Srinivasan et al. . |
| 5,602,557 | 2/1997 | Duerr . |
| 5,696,449 | 12/1997 | Boskamp . |
| 5,699,802 | 12/1997 | Duerr . |
| 5,702,405 | 12/1997 | Heywang-Koebrunner . |
| 5,706,812 | 1/1998 | Strenk et al. . |
| 6,029,082 * | 2/2000 | Srinivasan et al. ................... 600/422 |

OTHER PUBLICATIONS

Chen, C.–N. et al., "Quadrature Detection Coils—A Further √2 Improvement in Sensitivity", Journal of Magnetic Resonance 54, 1983, pp. 324–327.

Daniel, B.L. et al., "Interactive MR–Guided, 14–Gauge Core–Needle Biopsy of Enhancing Lesions in a Breast Phantom Mode", Acad Radiol, vol. 4, No. 7, Jul. 1997, pp. 508–512.

(List continued on next page.)

*Primary Examiner*—Brian L. Casler
(74) *Attorney, Agent, or Firm*—Nixon & Vanderhye P.C.

(57) ABSTRACT

An RF quadrature detection coil for interventional MRI comprises two nested orthogonal coils having generally rectangular shape in profile, each coil providing one "channel" of signal for quadrature detection. Each rectangular coil has two conductor windings and a common side in which the two conductors along that side are displaced apart in a common plane orthogonal to the plane of the coil to form a circular opening. The two individual coils are configured such that their rectangular conductor winding portions lie in planes perpendicular to each other but their arcuate conductor winding portions coincide in the same plane. Four paralleled conductors are arranged around the shared circular opening while two paralleled conductors form the three sides of the rectangular portion of each individual coil. With this arrangement, the circular opening allows for entry of a body part for MR imaging while the spaces between the orthogonal rectangular sides of the two coils provide large open access areas for one or more instruments during interventional procedures.

8 Claims, 6 Drawing Sheets

OTHER PUBLICATIONS

Fischer, Uwe, MD et al., "MR–Guided Biopsy of Suspect Breast Lesions with a Simple Stereotaxic Add–On Device for Surface Coils", Radiology, vol. 192, No. 1, Jul. 1994, pp. 272–273.

Fischer, Uwe, MD et al., "MR Imaging–Guided Breast Intervention: Experience with Two Systems", Radiology, vol. 195, May 1995, pp. 533–538.

Gould, Stuart W.T. et al., "Interventional MR–Guided Excisional Biopsy of Breast Lesions", Journal of Magn Reson Imaging, vol. 8, No. 1, Jan./Feb. 1998, pp. 26–30.

Harms, Steven E. et al., "Magnetic Resonance Imaging of the Breast", Magnetic Resonance Quarterly, vol. 8, No. 3, Sep. 1992, pp. 139–155.

Heywang–Köbrunner, Sylvia H. et al., "Prototype Breast Coil for MR–Guided Needle Localization", Journal of Computer Assisted Tomography, vol. 18, No. 6, Nov./Dec. 1994, pp. 876–881.

Hoult, D. I. et al., "Quadrature Detection in the Laboratory Frame", Magnetic Resonance in Medicine vol. 1, Sep. 1984, pp. 339–353.

Hyde, James S., "Quadrature Detection Surface Coil", Magnetic Resonance in Medicine, vol. 4, Feb. 1987, pp. 179–184.

Kandarpa, K. et al., "Prototype Miniature Endoluminal MR Imaging Catheter", J Vasc Interv Radiol, vol. 4, No. 3, May 1993, pp. 419–427.

Muller–Schimpfle, M. et al., "Precise MR–Guided Preoperative Marking of Breast Lesions with an Embolization Coil Using a Standard MR Coil", Rofo Fortschr Geb Rontgenstr Neuen Bildgeb Verfahr, vol. 168, No. 2, Feb. 1998, pp. 195–199.

Orel, Susan G., MD et al., "MR Imaging–Guided Localization and Biopsy of Breast Lesions: Initial Experience", Radiology, vol. 193, No. 1, Oct. 1994, pp. 97–102.

Redpath, Thomas W., "Quadrature rf Coil Pairs", Magnetic Resonance in Medicine, vol. 3, 1986, pp. 118–119.

Schenck, John F. et al., "Superconducting Open–Configuration MR Imaging System for Image–Guided Therapy", Radiology, vol. 195, Jun. 1995, pp. 805–814.

Schnall, Mitchell D., MD et al., "MR Guided Biopsy of the Breast", MRI Clinics of North America, vol. 2, No. 4, Nov. 1994, pp. 585–589.

Silverman, Stuart G., MD et al., "Interactive MR–Guided Biopsy in an Open–Configuration MR Imaging System", Radiology, vol. 197, No. 1, Oct. 1995, pp. 175–181.

Steiner, P. et al., "Interactive Stereotaxic Interventions in Superconducting, Open 0.5–Tesla MRI Tomography", Rofo Fortschr Geb Rontgenstr Neuen Bildgeb Verfahr, vol. 165, No. 3, Sep. 1996, pp. 276–280.

Stolier, Alan J., MD et al., "The Impact of Image–Directed Core Biopsy on the Practice of Breast Surgery: A New Algorithm for a Changing Technology", The American Surgeon, vol. 63, Sep. 1997, pp. 827–830.

Thiele, J. et al., "New Method of MR–Guided Mammary Biopsy", Rofo Fortschr Geb Rontgenstr Neuen Bildgeb Verfahr, vol. 168, No. 4, Apr. 1998, pp. 374–379.

* cited by examiner (Top View)

(Bottom View)

QUADRATURE DETECTION COIL FOR INTERVENTIONAL MRI

CROSS-REFERENCE TO RELATED APPLICATION

This application is related to (and incorporates by reference the entirety of) commonly-assigned co-pending U.S. application Ser. No. 09/198,967 to Sunyu Su, entitled "Open Structure Breast Coil And Support Arrangement For Interventional MRI" (N&V ref no. 202-75), filed Nov. 25, 1998.

FIELD OF THE INVENTION

This invention relates to an RF quadrature detection (QD) for magnetic resonance imaging (MRI) procedures. More specifically, it relates to an MRI quadrature detection coil having an open structural arrangement that allows easy access to body tissues during interventional MRI procedures (e.g., tissue biopsy or surgery).

BACKGROUND OF THE INVENTION

Magnetic resonance (MR) images acquired during surgery assist a surgeon to accurately locate tissue malignancies, obtain a biopsy from desired surgical sites on the patient, and assist in the successful removal of tissue from the patient. Interventional MRI is the magnetic resonance imaging technique (often involving real-time imaging) that allows a surgeon to perform MRI-guided tissue biopsy or surgical procedures.

To provide a surgeon with open access to surgical sites during MR imaging, conventional MR reception coils often have to sacrifice their signal reception performance. For interventional MRI guided surgery, it is desirable that the MR reception coil have a large opening to receive the body part to be imaged and wide-open access to provide a surgeon access to the surgical site with a biopsy needle or other surgical devices. To provide open surgical access, conventional interventional MRI coils generally have had a simplified RF coil structure. These simplified coils have large openings and provide good access during surgery. However, these simple coils also have compromised field homogeneity and signal reception efficiency. Because of these shortcomings, conventional interventional MRI reception coils have had limited usefulness as viable surgical tools.

An example of a simplified coil configuration previously used in interventional MRI is a flat single-loop surface coil arrangement used to image breasts. The flat signal-loop coil typically is placed near the chest wall of the patient, and around all or at least a portion of a single breast. A significant disadvantage of such a single-loop coil is that it has poor field homogeneity, and provides poor signal quality, especially with respect to breast tissue not immediately adjacent the RF reception coil loop. When using a single-loop reception coil, a surgeon experiences difficulty in clearly viewing or positively identifying malignancies of the breast that are more than a short distance from the RF coil.

Improving coil performance, such as the signal-to-noise ratio and uniformity of interventional MR reception coils, would increase the depth to which tissue can be clearly imaged. If the signal reception efficiency could be improved, then signal quality would be improved and good, clear interventional MR images would be available of the surgical site and surrounding tissue. Providing a clear image of a surgical or biopsy site would allow a surgeon to make better informed decisions during MRI guided surgery.

RF quadrature detection coil can improve signal detection efficiencies effectively. A quadrature detection coil arrangement consists of two orthogonal RF reception coils. If the two coils are resonant at the same frequency, then MR signals induced in one coil (channel A) will have a 90° phase shift with respect to the signals induced in the other coil (channel B).

In an MRI quadrature detection arrangement, a pair of MR signals (one from each coil-channel) are processed and combined to obtain one combined MR signal having a better signal-to-noise ratio than either of the single signals from the individual coil-channels of the quadrature arrangement. Where the two coils of the quadrature detection arrangement are identical (except for their orientation), the resultant signal should be about 40% better than that of either coil individually or of an equivalent single-loop coil arrangement.

While quadrature detection coils offer superior signal efficiency, they have in the past been difficult for use in interventional MRI devices. Providing open access to a tissue site is a significant constraint on the design of interventional quadrature detection coil. Compared to open structure single channel RF reception coils, the structure of a quadrature detection coil (having a pair of orthogonal coils) is more complex. The structural constraints of a quadrature coil arrangement present an imposing and perplexing problem which has made quadrature coils less applicable to interventional MRI, at least until the present invention.

SUMMARY OF THE INVENTION

In accordance with the present invention, an interventional MRI quadrature detection coil has been developed that has an open structural arrangement for providing both an opening to receive a breast (or other body part) to be imaged and provides open access to the tissues being imaged during surgery. In addition, the superior efficiency of quadrature coils of the present invention produces the good signal and image qualities that are characteristic of quadrature detection coils.

The quadrature detection coil of the present invention comprises a pair of orthogonal RF reception coils, that together form a generally-rectangular (box-like) shape. Each coil provides one signal channel of the two 90°-phase-shifted signal channels used for quadrature detection. In addition, each conductive-coil is arranged to have a pair of straight parallel sections, where each straight section is formed of two parallel and adjacent conductors. The four straight sections of the pair of coils form the four side edges of the rectangular shape of the quadrature detector. The two side-edges form by each coil are diagonal from each other across the rectangle, and are in a common side-edge plane. The common side-edge plane for one coil is perpendicular to the side-edge plane for the other coil. In addition, the two side-edge sections of each coil are connected by a semi-circular arc-shaped section of the coil. When the pair of coils are arranged together the arc-shaped sections of the pair of coils are in a plane perpendicular to the planes of the straight side-edge sections of the coils.

In the quadrature detection coil of the present invention, the circular opening formed by the arc-shaped portions of the coils provides an opening for a body part (such as a breast) to be imaged. In addition, the open side-walls between the side-edge straight portions of the coils provide large open access portals through which can pass surgical instruments used during interventional MRI procedures. Accordingly, a quadrature detection coil arrangement has been developed that combine superior signal efficiencies and open surgical access through the coils during interventional MRI procedures.

In a second embodiment of the present invention, the coil conductors are arranged to form circular openings on both the top and bottom ends of the rectangular structure formed by the straight side-edges sections of quadrature detection coil. By forming circular openings (aperture) in the top and bottom of the quadrature detection coils, a cylindrical passageway is formed through the entire coil structure. The cylindrical passageway is a highly open structure that facilitates interventional MRI of head, extremities and other body parts, and provides good signal efficiency.

Accordingly, a first embodiment of the invention is an RF quadrature receiving coil apparatus for interventional magnetic resonance imaging (MRI) comprising:

a pair of nested conductive coils each providing one of two channels for the RF quadrature receiving coil apparatus, an aperture in the nested conductive coils to receive a body part to be imaged;

wherein each coil has two parallel straight coil segments and each straight coil segment includes at least two adjacent coil windings, and the parallel straight coil segments of the nested coils are arranged at ninety degree (90°) intervals around the aperture, and the windings of the parallel straight coil segments are connected by arc-shaped coil winding segments forming a portion of a periphery of the aperture.

Another embodiment of the invention is an RF quadrature detection coil for interventional MRI, comprising:

a pair of nested conductive coils each having at least two windings and each coil providing one of two channels for the RF quadrature receiving coil apparatus, a printed circuit board having an aperture into the nested conductive coils to receive a body part to be imaged;

wherein each coil has two parallel straight coil segments and each straight coil segment has least two adjacent coil windings, and the parallel straight coil segments of the nested coils are perpendicular to the printed circuit board and are arranged at ninety degree (90°) intervals around the aperture, and the windings of the parallel straight coil segments are electrically connected to arc-shaped conductive strips on the printed circuit board.

BRIEF DESCRIPTION OF THE DRAWINGS

The structure and operation of the present invention will be more fully understood by careful study of the following detailed description of the presently preferred embodiment with particular reference to the accompanying drawings, wherein.

DETAILED DESCRIPTION OF THE PRESENTLY-PREFERRED EMBODIMENT

Figure 1:
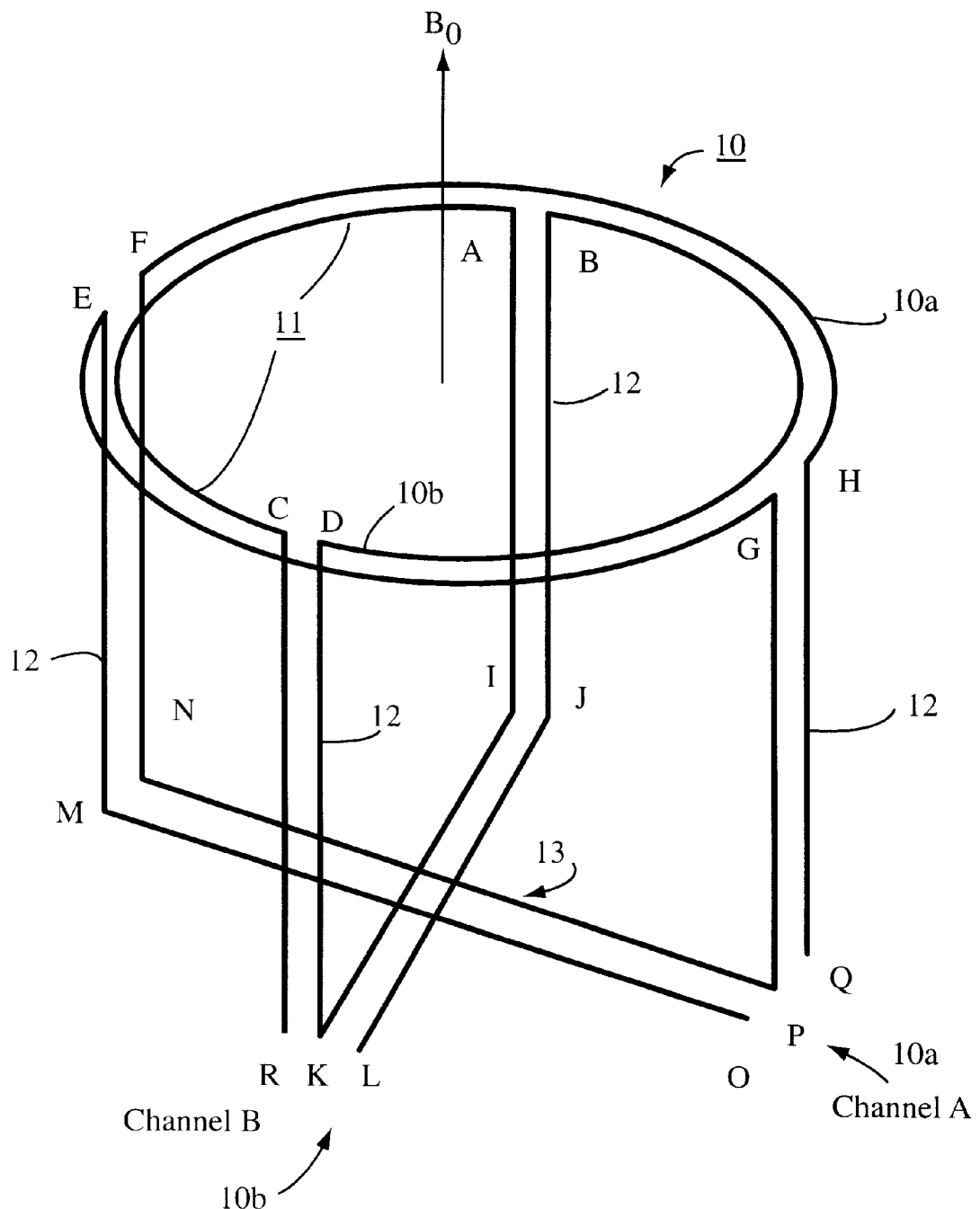
FIG. 1 is a schematic drawing of a MR quadrature detection coil arrangement having a pair of RF reception coils, in accordance with a first embodiment of the present invention.
Figure 2:
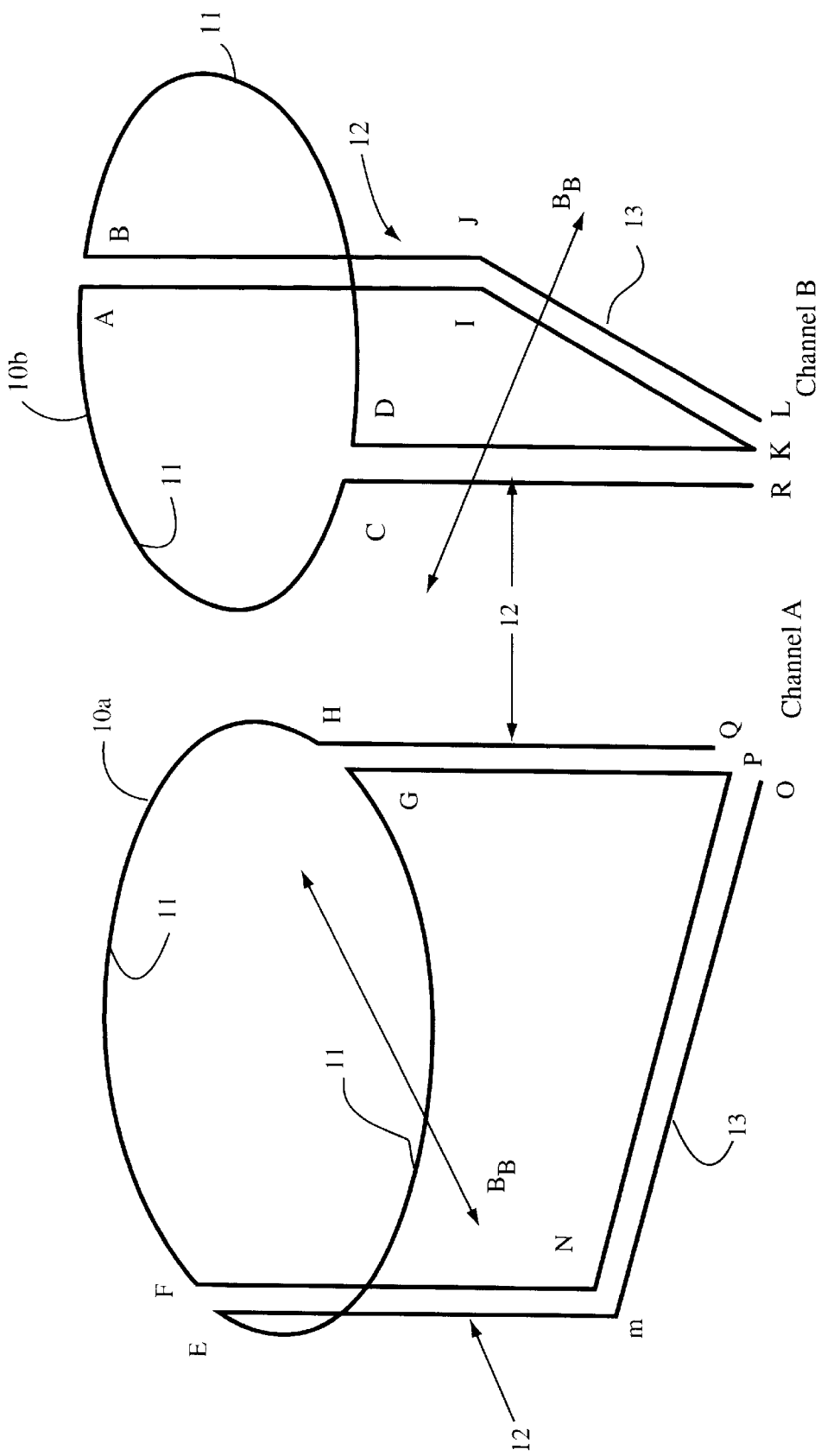
FIG. 2 is a schematic drawing of the detection coil arrangement shown in FIG. 1, in which the two RF reception coils of the arrangement are separated for purposes of illustration.

FIGS. 1 and 2 show schematically the conductive RF reception coil windings 10a, 10b, that form a quadrature detection coil pair 10. The conductor winding arrangement for each coil 10a, 10b, has three basic conductor coil sections, which are a top arcuate section 11, a pair of twin-conductor, straight sided sections 12, and a bottom section 13. The coil winding conductors of arcuate section 11 may be arranged to form a semi-circle 11. When the pair of coils 10a, 10b, are arranged as a quadrature detector 10, the semi-circular coil sections 11 form a large circular opening suitable for receiving a body part (such as a breast) for interventional MR imaging. Alternatively the arcuate section 11 of each coil may be have an elliptical, bowed rectangular or other geometrical shape that allows for an oval, rectangular, or other shaped opening in the quadrature detection coils to receive a body part to be imaged.

The coils 10a, 10b, each has two leads for signal reception. In coil 10a, leads O and Q correspond to the input and output terminals for the first channel (A) of the quadrature detector 10. Likewise, in coil 10b, leads R and L correspond to the input and output terminals, respectively, for the second channel (B) of the quadrature detection coil 10. From these terminals, MRI signals are sent to conventional MRI signal processing instrumentation.

The structural configuration and current path for the first coil 10a, (channel A), is represented by the coil segments connecting points O, M, E, G, P, N, F, H and Q, shown on FIGS. 1 and 2. The structural configuration and current path for the second coil 10b, (channel B), is represented by the coil segments connecting points R, C, A, I, K, D, B, J and L. In each coil, the coil segments form a conductive path which carries induced MR signals emitted by body tissue. In each coil, the straight sided coil segments are paired together. Coil segment C–R is paired with D–K, A–I with B–J in coil 10b, and, in coil 10a, segment Q–H is paired with G–P and E–M is with F–N.

Coil channel A is used to generate a magnetic field $B_A$ perpendicular to a plane defined by points FHQN, and channel B generates a magnetic field $B_B$ perpendicular to a plane defined by points ACRI. Since both $B_A$ and $B_B$ are perpendicular to static magnetic field $B_O$, the quadrature detection coil can be efficient in MR signal detection.

Figure 3:
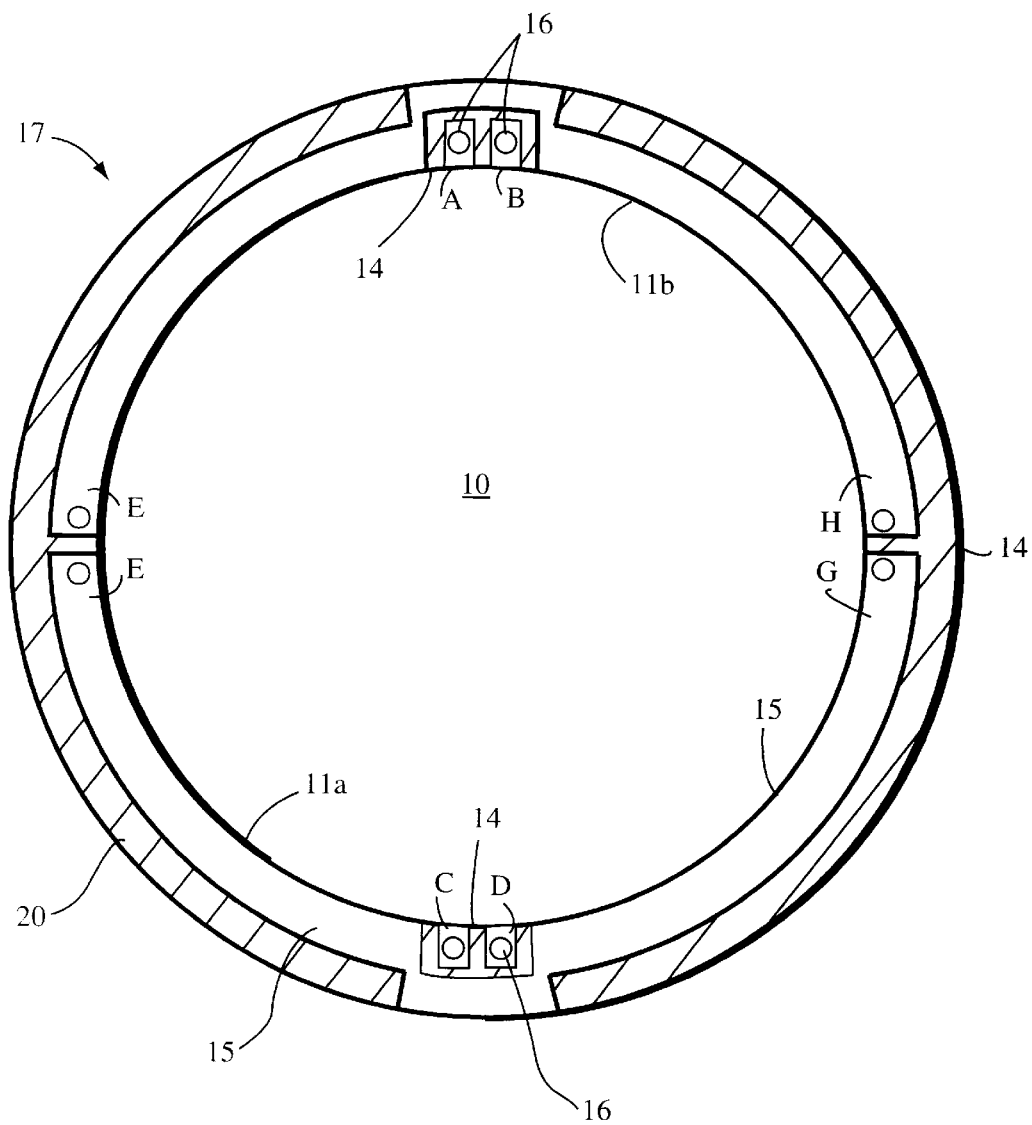
FIG. 3 is a top plan view of an exemplary annular double-sided PC board having arc-shaped sections of conductive strip comprising a portion of a first channel coil of a MRI quadrature detection coil in accordance with the first embodiment.
Figure 4:
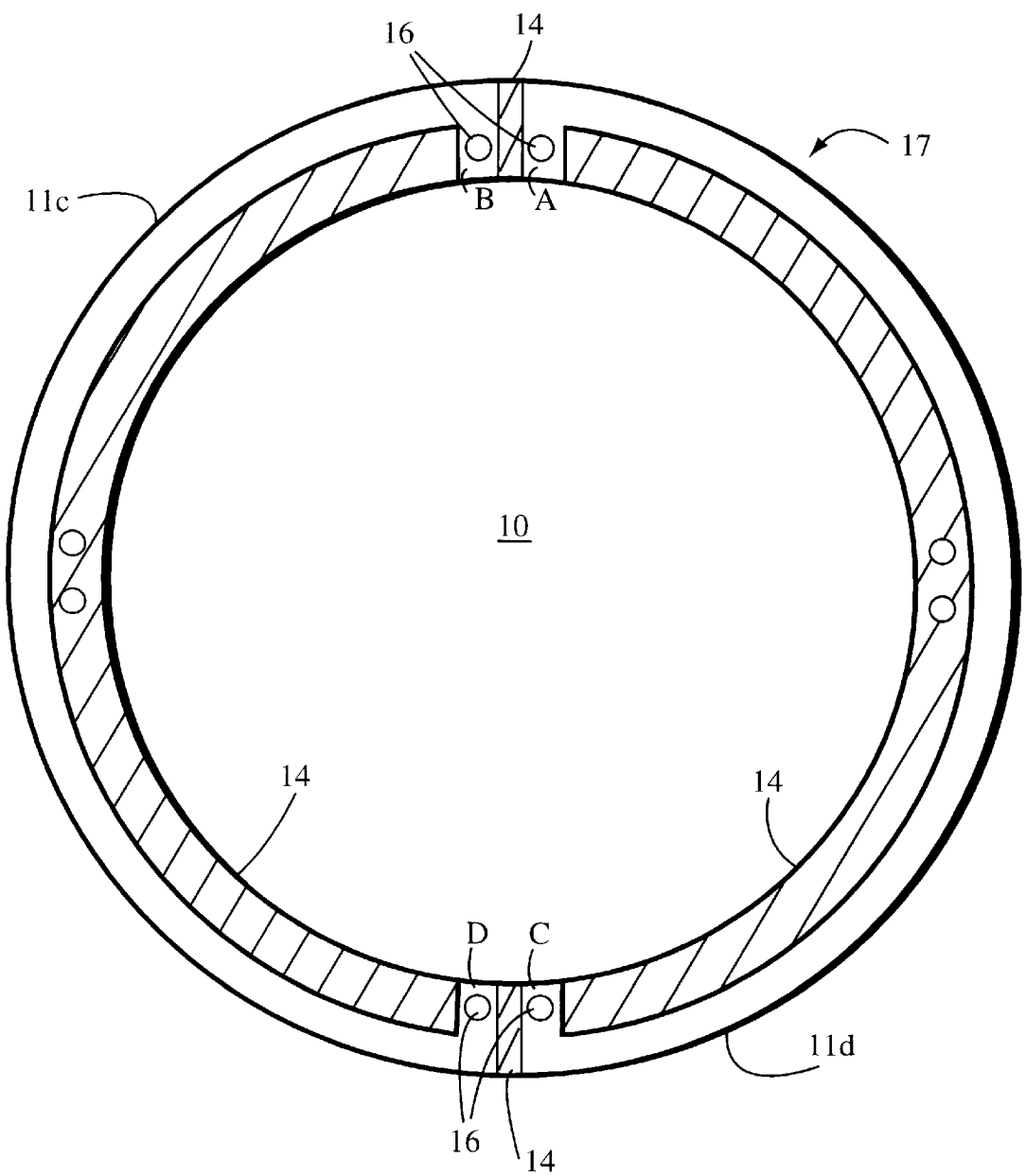
FIG. 4 is a bottom plan view of the annular double-sided PC board of FIG. 2, showing the arc-shaped sections of conductive coil comprising a portion of a second channel coil of a MRI quadrature detection coil.

FIG. 3 shows a top view of a ring-shaped, double-sided PC board 17, and FIG. 4 shows a bottom view of the PC board. While the PC board is shown as a disk for ease of illustration, the board may be a disk having upper and lower sides with arc-shaped coil winding segments or a ring having circumferential inner and outer sides with the winding segments. The PC board provides a supporting substrate for the semi-circular coil sections 11. These coil sections may be formed as copper foil-traces (11a, 11b, 11c, 11d) on the sides of the annular printed circuit (PC) board 17, as is illustrated in FIGS. 3 and 4. The use of a double-sided PC board as the semi-circular coil sections is a compact conductor arrangement that provides an open access to receive the body tissue to be positioned within the interior volume of the quadrature coil structure. In addition, the PC board and copper foil arrangement minimizes signal coupling (and interference) between the two channels A, B of the coils.

In FIGS. 3 and 4, the PC board is illustrate such that the shaded areas 14 are non-conductive areas of the annular board 17. On the top side of the PC board shown in FIG. 3, the conductive semi-circular strips 11a, 11b, correspond to arcuate coil segments EG and FH, respectively, of coil 10a. Similarly, copper strips 11c, 11d, on the bottom side of the PC board shown in FIG. 4 correspond to the two arcuate coil segments BD and AC, respectively, of coil 10b. These semi-circular coil segments on the PC board are connected to the straight segments 12 of their respective coils through pass-through holes 16 on the PC board. These pass throughholes have been labeled in FIGS. 3 and 4 to identify the connecting points (see FIGS. 1 and 2).

FIG. 4 illustrates the opposite side of the ring-shaped PC board 17, from the side shown in FIG. 3. The conductive semi-circular copper strips 11c, 11d, correspond to the arcuate segments BD and AC of coil 10b. The pass-through holes 16 provide solder connections between the foil strip segments 11c, 11d, and points A, B, C and D on the straight segments of coil 10b.

Figure 5:
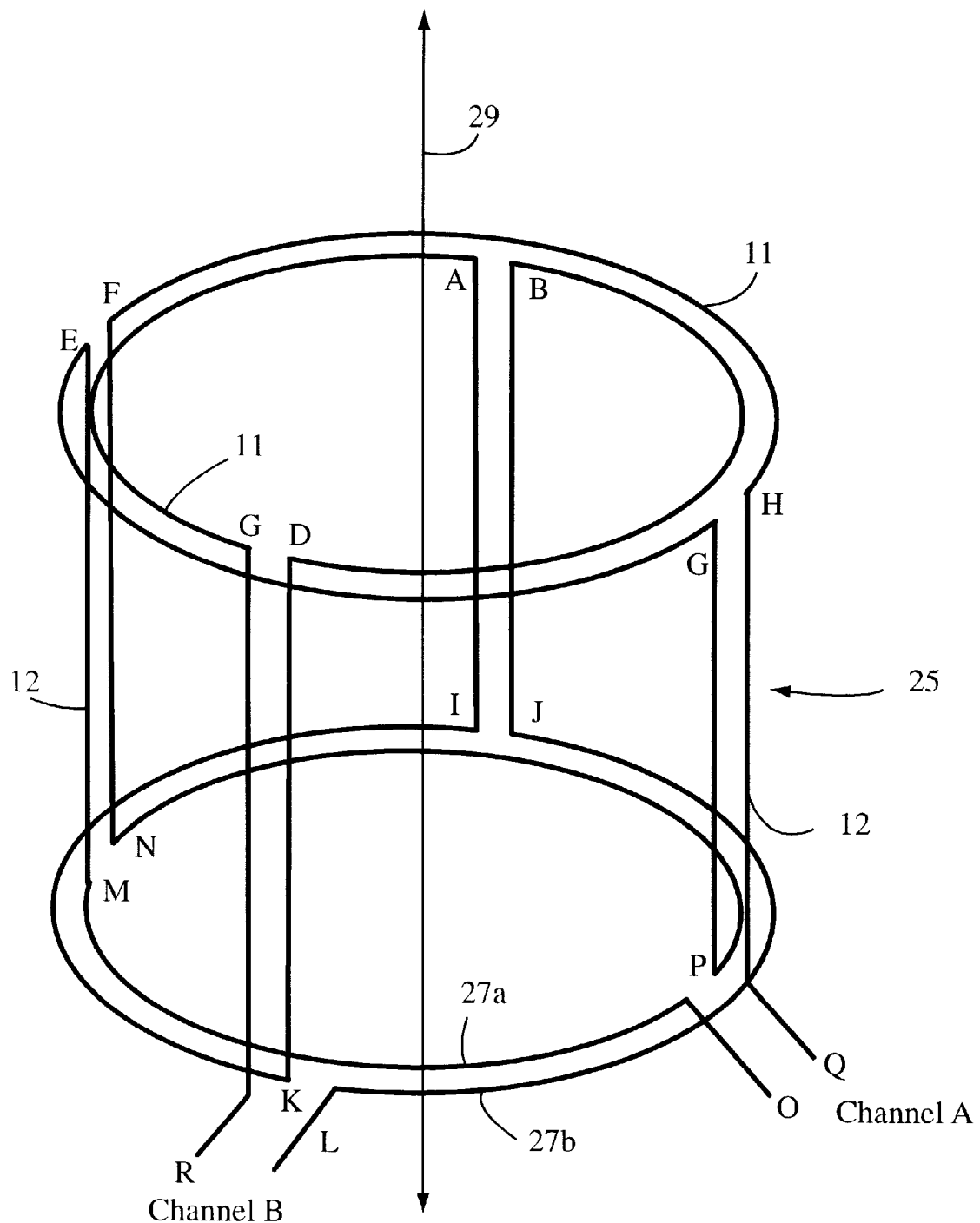
FIG. 5 is a schematic drawing of a MR quadrature detection coil arrangement having a pair of RF reception coils, in accordance with a second embodiment of the present invention.
Figure 6:
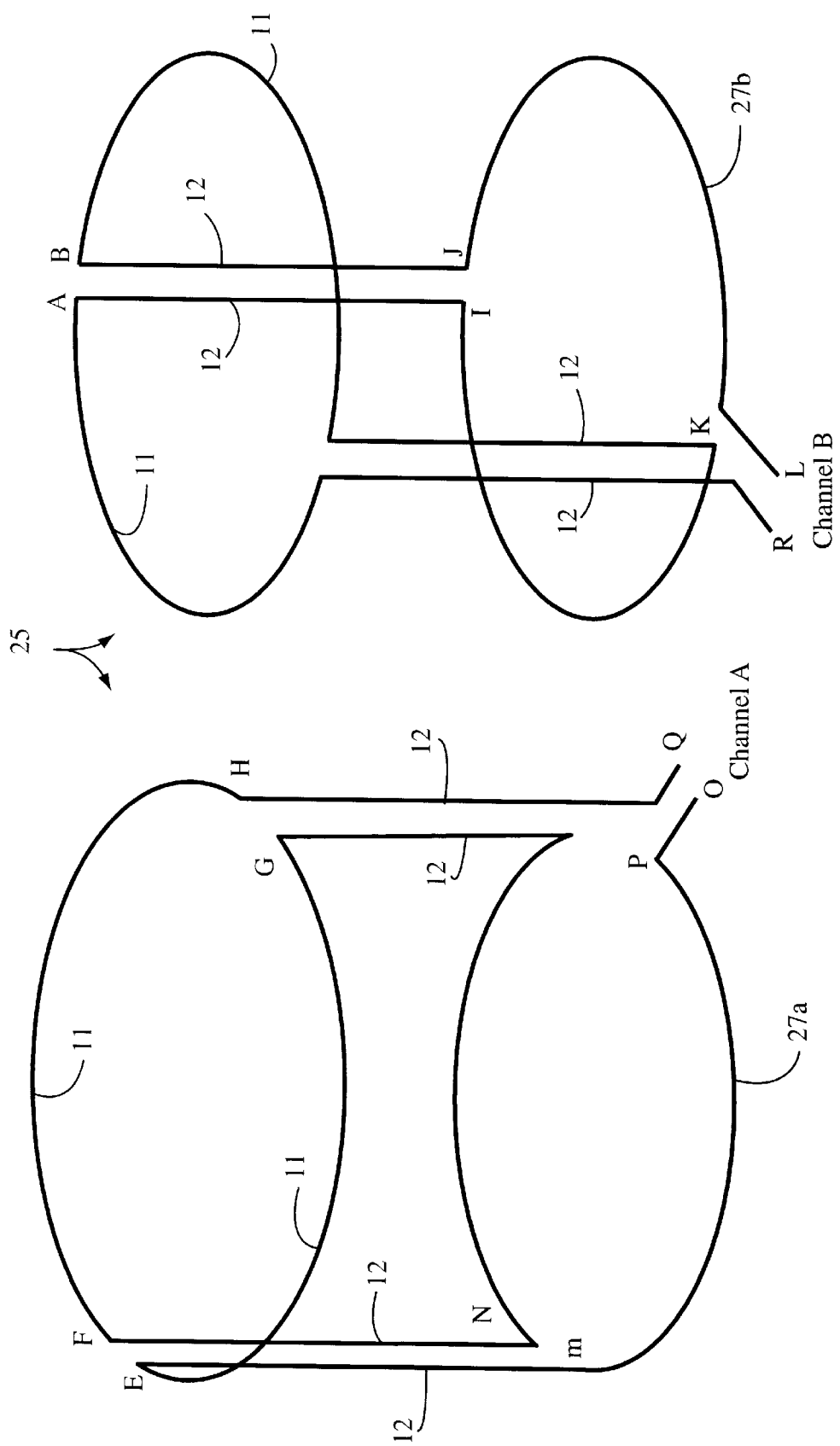
FIG. 6 is a schematic drawing of the detection coil arrangement shown in FIG. 5, in which the two RF reception coils of the arrangement are separated for purposes of illustration.

FIGS. 5 and 6 illustrate an alternative embodiment of the RF quadrature detection coil winding arrangement 25. A common referencing of numerals and letters have been used to the extent that the second embodiment is similar to the first detection coil winding arrangement 10. In this second arrangement 25, the conductor winding pairs 27a, 27b forming the bottom of the nested coil structure are bowed out to form two opposite semi-circular arcs that are displaced apart to form another circular opening (aperture). This bottom circular opening is coaxial 29 with the opening (semi-circular segments 11) in the opposite side of the quadrature detection coil. These circular openings in the nested coils provide a cylindrical passageway through the coils so that an object (such as a body part) may pass entirely through the coils.

The quadrature detection coil arrangement disclosed herein may be enclosed in a suitable open structure support frame. An exemplary support frame adapted for breasts is disclosed in co-pending U.S. application Ser. No. 09/198, 967 to Sunyu Su, entitled "Open Structure Breast Coil And Support Arrangement For Interventional MRI" (N&V ref no. 202-75).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An RF quadrature receiving coil apparatus for interventional magnetic resonance imaging (MRI) comprising:

a pair of nested conductive coils each providing one of two channels for the RF quadrature receiving coil apparatus, an aperture in the nested conductive coils adapted to receive a body part to be imaged;

wherein each coil has two parallel straight coil segments where each straight coil segment includes at least two adjacent coil windings, and the parallel straight coil segments of the nested coils are arranged at ninety degree (90°) intervals around the aperture, and the windings of the parallel straight coil segments are connected to arc-shaped coil winding segments forming a portion of a periphery of the aperture.

2. An RF quadrature receiving coil apparatus as set forth in claim 1 wherein the arc-shaped coil winding segments are conductive strips on an annular printed circuit board around the aperture.

3. An RF quadrature receiving coil apparatus as set forth in claim 1 wherein the parallel straight coil segments are in planes orthogonal to a plane containing the arc-shaped coil winding segments.

4. A quadrature detection coil as set forth in claim 1 wherein the arc-shaped coil winding segments of each coil are each semi-circular and are arranged together to form a circle around the aperture.

5. An RF quadrature detection coil for interventional MRI, comprising:

a pair of nested conductive coils each having at least two windings and each coil providing one of two channels for the RF quadrature receiving coil apparatus;

a printed circuit board having an aperture into the nested conductive coils adapted to receive a body part to be imaged;

wherein each coil has two parallel straight coil segments, and each straight coil segment has least two adjacent coil windings, and the parallel straight coil segments of the nested coils are perpendicular to the printed circuit board and are arranged at ninety degree (90°) intervals around the aperture, and the windings of the parallel straight coil segments are connected to arc-shaped conductive strips on the printed circuit board.

6. An RF quadrature detection coil as set forth in claim 5 further including a second printed circuit board having a second aperture coaxial to the first aperture, wherein the second printed circuit board includes arc-shaped conductive strips connecting the parallel straight coil segments.

7. An RF quadrature detection coil as set forth in claim 6 wherein the arc-shaped conductive strips connecting one coil are on an opposite side of the printed circuit board to the arc-shaped conductive foils connection the other coil.

8. An RF quadrature detection coil as set forth in claim 9 wherein the arc-shaped conductive strips for the one coil are arranged together to form a circle around the aperture in the printed circuit board.

* * * * *